United States Patent
Shimakawa et al.

(10) Patent No.: US 6,548,057 B1
(45) Date of Patent: Apr. 15, 2003

(54) BIFIDOBACTERIUM BREVE FERM BP 6223 FOR PRODUCING FERMENTED SOYMILK

(75) Inventors: Yasuhisa Shimakawa, Tokyo (JP); Takashi Morishita, Tokyo (JP); Fumiyasu Ishikawa, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/486,710

(22) PCT Filed: Aug. 11, 1998

(86) PCT No.: PCT/JP98/03562

§ 371 (c)(1), (2), (4) Date: Mar. 6, 2000

(87) PCT Pub. No.: WO99/11755

PCT Pub. Date: Mar. 11, 1999

(30) Foreign Application Priority Data

Sep. 4, 1997 (JP) .............................................. 9-239487

(51) Int. Cl.⁷ ............................. A23C 9/12; A23L 1/22; C12N 1/00; C12N 1/02; C12N 1/20
(52) U.S. Cl. .................... 424/93.4; 424/439; 435/252.1; 435/262; 435/822; 426/34; 426/49; 426/61
(58) Field of Search ............................ 435/252.1, 822, 435/252.4, 253.6, 260, 415, 426, 261; 426/34, 42, 49, 52, 7, 61; 724/93.4, 439

(56) References Cited

U.S. PATENT DOCUMENTS 5,443,951 A * 8/1995 Yamamoto et al. ............. 435/6

FOREIGN PATENT DOCUMENTS

| EP | 0 192 986 | 9/1986 |
| EP | 0 486 738 | 5/1992 |
| EP | 0974268 A1 * | 1/2000 |
| FR | 2 560 046 | 8/1985 |
| JP | 11-32764 * | 2/1999 |
| WO | WO98/35564 * | 8/1998 |

OTHER PUBLICATIONS

Matsuyama et al. "Fermentation Profiles & Util. of sugars of bifidobacteria in soymilk" J. of the Japenese Soc for Food Sci. & Tech., vol. 39, No. 10 see abstract only, 1992.*

Matsuyama et al, "Fermentation Profiles and Utilization of Sugars of Bifidobacteria in Soymilk," Nippon Shokuhin Kogyo Gakkaishi vil. 39, No. 10, 887–893 (1992).

Catalogue of Strains, Second Edition 1984, Japan Collection of Microorganisms.

Kenji Sakai, et al., Agricultural and Biological Chemistry, vol. 51, No. 2, pp. 315–322, "Hydrolysis of χ–D–Galactosyl Oligosaccharides in Soymilk by χ–D–Galactosidase of *Bifidobacterium breve* 203", 1987.

Jun Matsuyama, et al., Bulletin of the Faculty of Agriculture Tamagawa University, pp. 6–14, "Ulitilization of Oligosaccharides in Soymilk by Bifidobacteria and Lactic Acid Bacteria", 1987, (with English Summary).

JP, 9–201164, A (Yakult Honsha Co., Ltd.), Aug. 5, 1997 (Family: none).

JP, 8–66161, A (Kikkoman Corp.), Mar. 12, 1996 (Family: none).

JP, 4–320642, A (Snow Brand Rolly K.K., et al.), Nov. 11, 1992 (Family: none).

* cited by examiner

Primary Examiner—David M. Naff
Assistant Examiner—Deborah K. Ware
(74) Attorney, Agent, or Firm—Oblon, Spivak, McClelland, Maier & Neustadt, P.C.

(57) ABSTRACT

A *Bifidobacterium breve* strain provided is showing a viable count of $1 \times 10^9$ cells/ml or more immediately after culturing in a soymilk medium and sustaining a viable count of $1 \times 10^8$ cells/ml or more after storage at 10° C. for 14 days. The strain is preferably *Bifidobacterium breve* FERM BP-6223, and is used for producing fermented soymilk.

11 Claims, 2 Drawing Sheets

BIFIDOBACTERIUM BREVE FERM BP 6223 FOR PRODUCING FERMENTED SOYMILK

TECHNICAL FIELD

The present invention relates to *Bifidobacterium breve* which excellently survives storage, and to fermented soymilk of pleasant flavor containing the same.

BACKGROUND ART

Since long ago, fermentation of soymilk by use of microorganisms has been carried out in order to attain sensory improvement of soymilk, which has a characteristic bean odor and grassy taste. In the course of such fermentation treatment, a variety of microorganisms such as lactic acid bacteria, yeasts, *Bacillus natto*, acetic acid bacteria, and Aspergillus have been employed. It is reported that in most cases such treatment yields fermented products having pleasant flavor.

Soymilk has been known to promote proliferation of microorganisms which belong to genus Bifidobacterium (hereinafter referred to as bifidobacteria), possibly due to soybean oligosaccharide contained in soymilk (Yoichi KOBAYASHI et al., "Intestinal Flora and Food Factors," p69, 1984, published by Gakkai Shuppan Center).

Meanwhile, a number of studies have been conducted on usefulness of bifidobacteria. For example, administration of a live-bacterium preparation (*Bifidobacterium breve*) has proven to exhibit a curative effect on refractory pediatric diarrhea, and a possible mechanism thereof may be attributed to improvement of intestinal flora. Furthermore, it has been found that administration of the preparation to an adult results in reduction of putrefied products in feces and putrefied-product-producing bacteria. In addition, an immunoactivating effect of bifidobacteria has also been elucidated. Thus, bifidobacteria are considered to contribute to human health through improvement of the intestinal environment (edited by Tomotari MITSUOKA, "Study of Bifidobacteria," 1994).

Thus, a variety of products employing bifidobacteria have been developed, and simultaneously efforts have been made to develop a fermented soymilk product which contains numerous bifidobacteria and which also maintains a viable count (high survival rate) throughout the period required for product distribution.

However, since bifidobacteria generate lactic acid and acetic acid at a mole ratio of 1:1.5 through metabolism of sugar, bifidobacteria tend to perish by self-produced acid. Therefore, growth thereof to a certain viable count or higher and maintenance of the viable count are difficult.

In order to solve the aforementioned problem, employment of a bifidobacterium, of high survival rate has been proposed (Japanese Patent No. 2563197).

However, even though the employed bifidobacterium shows an improved survival rate as compared with that of a conventional bifidobacterium, the employed bacterium cannot be proliferated to a level of $1 \times 10^9$ cells/ml or higher, and maintenance of a viable count of at least $1 \times 10^8$ cells/ml after 14 days' storage is difficult.

Thus, an object of the present invention is to provide a bifidobacterium which can sustain a certain level of viable count even after storage for a certain period of time. Another object of the invention is to provide fermented soymilk containing the bifidobacterium.

DISCLOSURE OF THE INVENTION

In view of the foregoing, the present inventors have conducted earnest studies, and have discovered a bifidobacterium satisfying the aforementioned requirement for viable count and have also found that fermented soymilk of pleasant flavor and high viable count can be produced by use of the bifidobacterium. The present invention has been accomplished on the basis of these findings.

Accordingly, the present invention provides *Bifidobacterium breve* exhibiting a viable count of $1 \times 10^9$ cells/ml or more immediately after culturing in a soymilk medium and sustaining a viable count of $1 \times 10^8$ cells/ml or more after storage at 10° C. for 14 days. The invention also provides fermented soymilk containing the same.

BEST MODES FOR CARRYING OUT THE INVENTION

Figure 1:
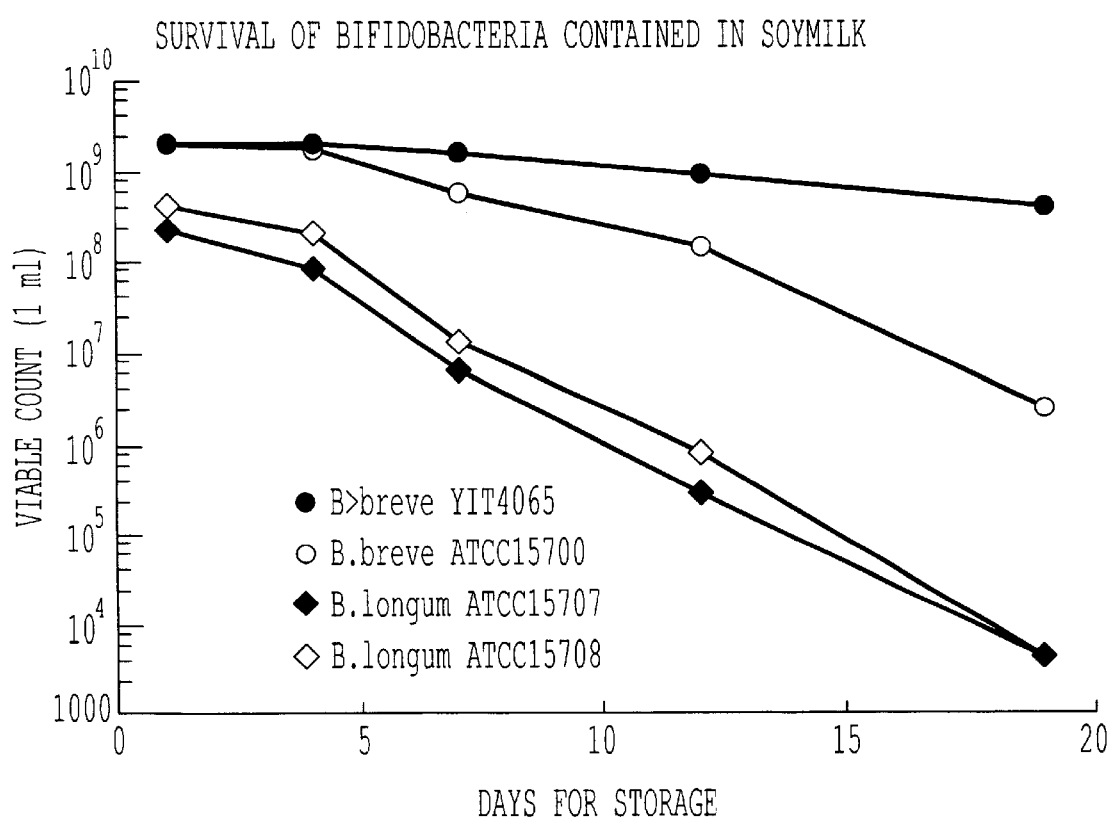
FIG. 1 is a graph showing survival of bacteria contained in soymilk.

The *Bifidobacterium breve* of the present invention exhibits a remarkably high survival rate in a soymilk medium and, after being grown to a level of $1 \times 10^9$ cells/ml, sustains a viable count of $1 \times 10^8$ cells/ml or more even after storage at 10° C. for 14 days.

Example microorganisms which belong to Bifidobacterium breve include a microorganism named YIT 4065 and deposited as FERM BP-6223 (original depository date: Feb. 29, 1996) to the National Institute of Bioscience and Human-Technology, Agency of Industrial Science and Technology (address: 1-3, Higashi 1-chome, Tsukuba-shi, Ibaraki-ken 305-0046 JAPAN) in accordance with the Budapest Treaty. The bacterium is produced in the following manner.

Cultured cells ($1.5 \times 10^9$ cells) of *Bifidobacterium breve* YIT 4006 deposited as FERM BP-752 (original depository date: Jan. 28, 1977) to the Fermentation Research Institute, Agency of Industrial Science and Technology, Ministry of International Trade and Industry (address: 1-3, Higashi 1-chome, Tsukuba-shi, Ibaraki-ken 305-0046 JAPAN) in accordance with the Budapest Treaty) are suspended in 50 mM phosphate buffer (pH 7.0), and an equiamount of a 5 µg/ml solution of NTG (N-methyl-N'-nitro-N-nitrosoguanidine) is mixed with the suspension. The resultant mixture is maintained at 37° C. for 30 minutes. After removal of NTG by washing, the resultant mutation-treated cells are inoculated to a 14% whole milk powder medium (yeast extract content: 0.03%) and cultured at 37° C. until the pH reaches 4.5–4.7. Fine liquor is added to the cultured product in an amount of 8%, and the mixture is poured into test tubes. Each test tube is sealed with a butyl rubber stopper and stored at 10° C. The viable count is measured over time by use of a modified Rogosa agar medium. When the viable count reaches about 1%, the stored product is inoculated again to a 14% whole milk powder medium (yeast extract content: 0.03%) and cultured at 37° C. until the pH reaches 4.5–4.7. After addition of sugar to the cultured product, the mixture is stored again. This procedure of storing-counting-inoculation-culturing is repeated four times, and from the thus-obtained fermented product, a strain showing improved survival is separated as *Bifidobacterium breve* YIT 4065.

In addition to the aforementioned survival property, *Bifidobacterium breve* YIT 4065exhibits the following mycological properties.

The bacterium is proven to be pleomorphic; i.e., rod-like or branching, through observation under an optical microscope, and is gram-positive. When the bacterium is anaerobic-cultured on a modified Rogosa agar medium, a white and glossy colony is formed, whereas when it is similarly cultured on a milk medium, lactic acid and acetic acid are formed to curdle milk. Catalase activity is negative.

The bacterium exhibits positive fermentation activity to ribose, fructose, galactose, sucrose, maltose, cellobiose, lactose, melibiose, raffinose, melezitose, and salicin and negative activity to arabinose, xylose, trehalose, mannitol, sorbitol, and inulin.

The fermented soymilk of the present invention can be produced through fermentation of soymilk by use of the aforementioned *Bifidobacterium breve*.

The soymilk serving as a raw material in the present invention is preferably produced from untreated soybeans containing oils and fats, defatted soybeans, soybean flakes, etc. Defatted soybeans may serve as a raw material.

Soymilk can be produced by dipping raw material in water; crushing with addition of hot water optionally containing 0.5–1.0 wt.% (hereinafter simply referred to "%") of sodium carbonate; removing okara (bean-curd refuse); and sterilizing with heat. However, production of soymilk is not limited to this method, and the soymilk used in the present invention may be produced in any manner.

To the soymilk, there may be added nutrients required for growing bacteria, such as sugar incorporated into food, e.g., sucrose, glucose, fructose or invertose; meat extract; peptone; yeast extract; and peptide in order to carry out post-treatment with a bacterium. In addition, in order to realize the optimal pH for a target bacterium, acids incorporated into food such as citric acid, malic acid, ascorbic acid, lactic acid, and acetic acid may be added to the soymilk.

No particular limitation is imposed on the method of fermentation, and fermentation may be carried out under typical conditions. For example, when *Bifidobacterium breve* YIT 4065 is inoculated to the aforementioned soymilk, culture may be carried out at 37° C. for approximately 20–22 hours until the pH reaches approximately 4.5–4.7. Fermentation may be carried out under conditions appropriately selected in accordance with culture conditions, such as standing culture, spinner culture, shaking culture, and aerobic culture.

Although the fermented soymilk of the present invention may be produced by adding *Bifidobacterium breve* to soymilk, other bifidobacteria or other microorganisms may further be added. Examples of such microorganisms include bacteria such as Lactobacillus, Lactococcus, Streptococcus, Leuconostoc, Bacillus, Acetobacter, and Gluconobacter; yeasts such as Saccharomyces, Candida, Rhodotorula, Pichia, Schizosaccharomyces, Torula, and Zygosaccharomyces; and filamentous fungi such as Aspergillus, Eurotium, Monascus, Mycol, Neurospora, Penicillium, and Rhizopus.

The thus-obtained fermented soymilk of the present invention may be serve as food as is or may be formed into an oral pharmaceutical, and may further contain any customarily-employed additive. Examples of such additives include saccharides, proteins, fats and oils, vitamins, plant extract, animal extract; bacterium extract; perfumes, and colorants. Furthermore, the fermented soymilk of the present invention may be processed into any form, such as liquid, paste, sponge, or solid. In addition to a soymilk beverage, the fermented soymilk may be processed into a variety of food products such as soymilk yogurt, soymilk pudding, and tofu (soybean curd).

EXAMPLES

The present invention will next be described in more detail by way of examples.

Example 1

Soymilk (product of Shikoku Kakoki, solid content 12.0%, crude fat 2.48%, crude protein 4.71%) was sterilized with steam at 100° C. for 90 minutes.

Subculture was carried out several times by use of soymilk produced under anaerobic conditions, to thereby produce two *Bifidobacterium breve* inocula and two *Bifidobacterium longum* inocula shown in FIG. 1. Each of these inocula was inoculated to the aforementioned sterilized soymilk in an amount of 0.5–2%, and cultured until the pH reached 4.6.

After addition of glucose to the fermented product in an amount of 5%, the mixture was stored at 10° C. under anaerobic conditions. Viable cells were counted, and the results are shown in FIG. 1.

Both *Bifidobacterium breve* samples showed a viable count of $1 \times 10^9$ cells/ml immediately after preparation of a fermented product. However, *Bifidobacterium breve* ATCC 15700 failed to sustain a viable count of $1 \times 10^8$ cells/ml after storage for 14 days.

Also, the two *Bifidobacterium longum* samples failed to sustain viable count.

The *Bifidobacterium breve* YIT 4065 (FERM BP-6223) of the present invention sustained a viable count of $1 \times 10^8$ cells/ml or more after storage, and provided fermented soymilk of excellent viable count and excellent survival rate.

Example 2

Soymilk (product of Shikoku Kakoki, solid content 12.0%, crude fat 2.78%, crude protein 5.03%) (7 L) was placed in a 10-L jar fermenter and sterilized with steam at 100° C. for 90 minutes.

Subculture was carried out several times by use of soymilk produced under anaerobic conditions, to thereby produce *Bifidobacterium breve* inocula. Each inoculum was inoculated in an amount of 0.5%, and cultured until the pH reached 5.3.

Figure 2:
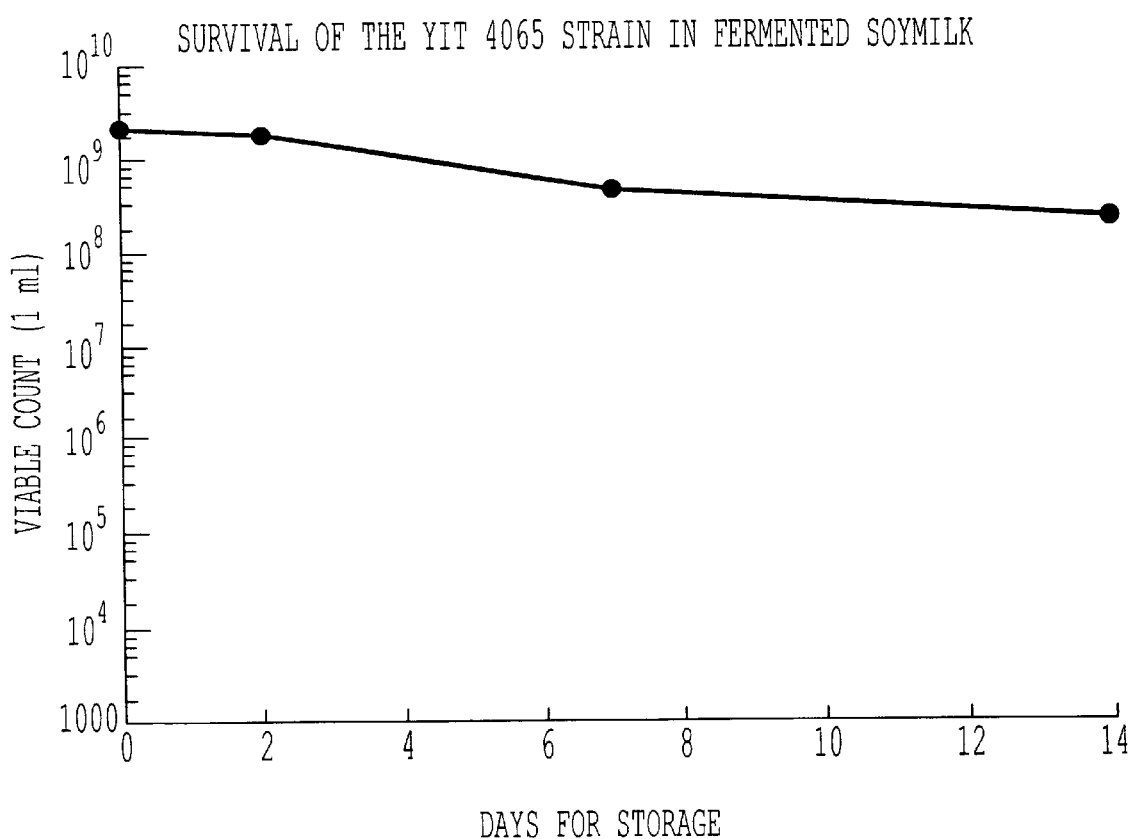
FIG. 2 is a graph showing survival of the YIT 4065 strain in fermented soymilk.

After addition of a syrup solution (1.5 L) containing aspartame (0.13%) and citric acid (1.1%) to the fermented product in an amount of 5%, the mixture was stored at 10° C. under anaerobic conditions. Viable cells were counted and flavor was investigated, and the results are shown in FIG. 2.

The *Bifidobacterium breve* YIT 4065 of the present invention sustained a viable count of $1 \times 10^8$ cells/ml or more after storage at 10° C. for 14 days, and the fermented soymilk produced by use of the same had excellent flavor.

INDUSTRIAL APPLICABILITY

The *Bifidobacterium breve* of the present invention exhibits an initial viable count of $1 \times 10^9$ cells/ml or more and sustainment of a viable count of $1 \times 10^8$ cells/ml or more after storage at 10° C. for 14 days, and thus is a remarkably excellent bifidobacterium which contributes to human health through improvement of the intestinal environment.

The fermented soymilk employing the *Bifidobacterium breve* of the present invention contains at high concentration a bifidobacterium which may have a variety of possible uses, and advantageously sustains viable count during storage without drastic reduction in the viable count.

What is claimed is:

1. A biologically pure culture of a *Bifidobacterium breve* strain FERM BP-6223.

2. A fermented soymilk comprising the *Bifidobacterium breve* as recited in claim 1.

3. The fermented soymilk of claim 2 further comprising one or more additives selected from the group consisting of sucrose, fructose, glucose, invertose, meat extract, peptone, and yeast extract.

4. The fermented soymilk of claim 2 further comprising one or more acids selected from the group consisting of citric acid, malic acid, ascorbic acid, lactic acid and acetic acid.

5. The fermented soymilk of claim 2 further comprising one or more additives selected from the group consisting of saccharides, proteins, fats, oils, vitamins, plant extract, animal extract, bacterium extract, perfume and colorant.

6. The fermented soymilk of claim 2 further comprising a microorganism selected from the group consisting of Lactobacillus, Streptococcus, Leuconostoc, Bacillus, Acetobacter, Gluconobacter, Saccharomyces, Candida, Rhodotorula, Pichia, Schizosaccharomyces, Torula, Zygosaccharomyces, Aspergillus, Eurotium, Monascus, Mycol, Neurospora, Penicillium, and Rhizopus.

7. A method of producing a fermented soymilk comprising fermenting soymilk with the *Bifidobacterium breve* strain of claim 1.

8. The method of claim 7, which further comprises adding one or more additives selected from the group consisting of sucrose, fructose, glucose, invertose, meat extract, peptone, and yeast extract.

9. The method of claim 7, which further comprises adding one or more acids selected from the group consisting of citric acid, malic acid, ascorbic acid, lactic acid and acetic acid.

10. The method of claim 7, which further comprises adding one or more additives selected from the group consisting of saccharides, proteins, fats, oils, vitamins, plant extract, animal extract, bacterium extract, perfume and colorant.

11. The method of claim 7, which further comprises adding a microorganism selected from the group consisting of Lactobacillus, Streptococcus, Leuconostoc, Bacillus, Acetobacter, Gluconobacter, Saccharomyces, Candida, Rhodotorula, Pichia, Schizosaccharomyces, Torula, Zygosaccharomyces, Aspergillus, Eurotium, Monascus, Mycol, Neurospora, Penicillium, and Rhizopus.

* * * * *